United States Patent
Oertling et al.

(10) Patent No.: US 8,242,289 B2
(45) Date of Patent: Aug. 14, 2012

(54) ALKYL-SUBSTITUTED TETRAHYDROPYRANS AS FLAVORING SUBSTANCES

(75) Inventors: Heiko Oertling, Holzminden (DE); Constanze Brocke, Groβ-Gerau (DE); Hubert Loges, Hoxter (DE); Arnold Machinek, Holzminden (DE)

(73) Assignee: SYMRISE AG, Holzminden (DE)

( * ) Notice: Subject to any disclaimer, the term of this patent is extended or adjusted under 35 U.S.C. 154(b) by 407 days.

(21) Appl. No.: 12/696,200

(22) Filed: Jan. 29, 2010

(65) Prior Publication Data
US 2010/0226864 A1    Sep. 9, 2010

Related U.S. Application Data

(60) Provisional application No. 61/158,162, filed on Mar. 6, 2009.

(51) Int. Cl.
*C07D 309/00* (2006.01)
*C07D 315/00* (2006.01)

(52) U.S. Cl. ......... 549/356; 549/416; 549/423; 549/425

(58) Field of Classification Search .................. 549/356, 549/416, 423, 425
See application file for complete search history.

(56) References Cited

U.S. PATENT DOCUMENTS

| | | | |
|---|---|---|---|
| 4,518,615 A | 5/1985 | Cherukuri et al. |
| 5,002,791 A | 3/1991 | Knebl |
| 5,093,136 A | 3/1992 | Panhorst et al. |
| 5,137,741 A | 8/1992 | Zampino et al. |
| 5,266,336 A | 11/1993 | McGrew et al. |
| 5,458,894 A | 10/1995 | Knebl et al. |
| 5,589,158 A | 12/1996 | Mankoo |
| 5,601,858 A | 2/1997 | Mansukhani et al. |
| 6,432,441 B1 | 8/2002 | Bealin-Kelly et al. |
| 6,986,709 B2 | 1/2006 | Hughs-Baird et al. |
| 2004/0241312 A1 | 12/2004 | Gatfield et al. |

FOREIGN PATENT DOCUMENTS

| | | |
|---|---|---|
| DE | 10225350 A1 | 12/2003 |
| DE | 69824198 T2 | 9/2004 |
| DE | 10351422 A1 | 6/2005 |
| EP | 242325 A2 | 10/1987 |
| EP | 1847181 A1 | 10/2007 |
| WO | WO-0241861 A1 | 5/2002 |
| WO | WO-2004000787 A2 | 12/2003 |
| WO | WO-2004050069 A1 | 6/2004 |
| WO | WO-2008138162 A1 | 11/2008 |

OTHER PUBLICATIONS

Voitsekhovskaya, A.L., et al., "Substituted lactones and their transformations. VII. Synthesis of 2-methyl-3-alkyltetrahydropyrans and 3-alkyl-2, 6-hexanediols by reduction of .delta.-methyl-.gamma.-alkyl-.delta.-valerolactones," Database Caplus [Online] Chemical Abstracts Service, 1967, XP002582475.
Kula Jozef et al., "Tetrahydrofuran and Tetrahydropyran Derivatives as Odor Substances," Perfumer and Flavorist, vol. 17. No. 5, 1992, pp. 77-79, 82, 84-86, and 88-92 XP009133547.
European Search Report, European Application No. 09176696.4, received on Jun. 28, 2010.

*Primary Examiner* — Andrew D Kosar
*Assistant Examiner* — Raymond Covington
(74) *Attorney, Agent, or Firm* — Connolly Bove Lodge & Hutz LLP

(57) ABSTRACT

The present invention relates to alkyl-substituted tetrahydropyrans, mixtures containing these alkyl-substituted tetrahydropyrans, their respective use and corresponding flavored products.

21 Claims, 1 Drawing Sheet

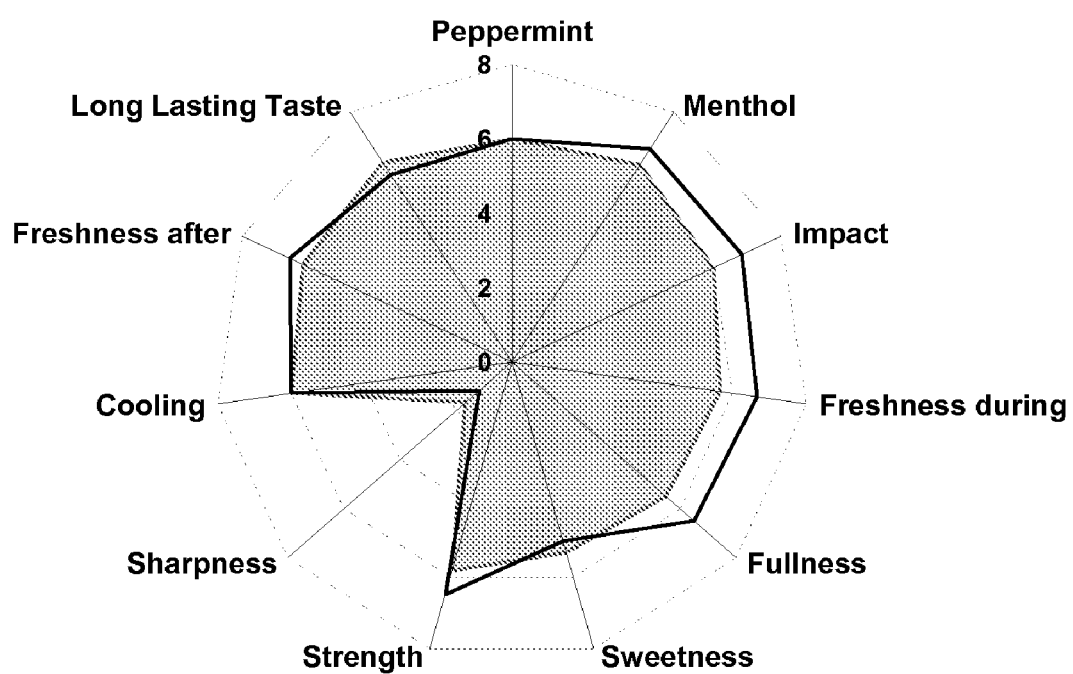

ALKYL-SUBSTITUTED TETRAHYDROPYRANS AS FLAVORING SUBSTANCES

CROSS REFERENCE TO RELATED APPLICATIONS

This nonprovisional application claims priority under 35 U.S.C. §119(e) on U.S. Provisional Application No. 61/158,162 filed on Mar. 6, 2009, the entire contents of which is hereby incorporated by reference.

The present invention relates to alkyl-substituted tetrahydropyrans of the following formula (I), mixtures containing these alkyl-substituted tetrahydropyrans, their respective use and corresponding flavored products.

In a particular embodiment the invention relates to the use of these flavoring substances in flavoring substance and flavoring compositions with a freshening effect for use in oral hygiene products.

The invention also relates to preparations and nasal preparations which bring about in the mouth, throat and respiratory tract a fresh and relieving feeling and preparations containing these compounds.

In order to meet the constant demand from consumers for constant new smell and taste experiences, in the flavoring substance and flavoring industry there is a demand for substances which have exceptional sensorial characteristics (i.e. that can be perceived with the senses) and with which notable novel effects can be achieved. Here, apart from the pure smell and taste characteristics other additional characteristics may be important, so that for example the smell and taste sensations can be inhibited or intensified.

Flavoring substance or flavoring compositions with a freshening effect give for example oral hygiene products such as toothpastes and mouthwashes, and confectionery such as candies and chewing gum, their typical fresh taste which is perceived as pleasant.

Substances which are used on a large scale for the manufacture of such flavoring substance or flavoring compositions with a freshening effect are for example eucalyptol (1,8-cineol) and menthol. The use of these substances, however, is associated with a number of disadvantages. Thus eucalyptol, apart from its freshening effect, has a very strong characteristic medicinal taste, which many consumers find off-putting, particularly if the eucalyptol is used in high doses. When menthol is used the freshening effect starts with a certain delay, and at high doses the menthol develops a bitter-sharp characteristic taste which has a rather unpleasant effect.

The main object of the present invention was therefore to indicate compounds or mixtures of compounds, which in flavoring substance or flavoring compositions with a freshening effect, lead to an enhanced, rapidly perceptible freshening experience. In addition the compounds or compound mixtures to be indicated should preferably exhibit the weakest possible characteristic taste, in particular little or no medicinal and/or bitter taste.

The new tetrahydropyrans according to the invention exhibit an effect akin to that of 1,8-cineol (eucalyptol) with regard to achieving a fresh relieving feeling in the mouth, pharyngeal cavity and respiratory tract, but without generating an unpleasant taste sensation.

The tetrahydropyrans according to the invention are essentially characterized by a neutral, fresh and cool taste. They are therefore eminently suitable for use in flavoring substance and flavoring compositions. They have a notable ability in flavoring substance and flavoring compositions to increase the intensity and force of the feeling of freshness.

The effect of generating a fresh relieving feeling in the mouth, pharyngeal cavity and respiratory tract applies to the alkylated tetrahydropyrans according to the invention in all isomeric forms, for example diastereomers and enantiomers.

According to the invention, therefore, an alkylated tetrahydropyran of formula (I) is indicated:

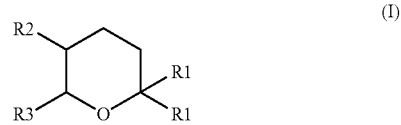

in which
each R1 independently of the other is either
hydrogen
or a branched or unbranched alkyl residue with between 1 and 3 C-atoms
or a branched or unbranched alkenyl residue with between 2 and 3 C-atoms,
and R2 is a branched or unbranched alkyl or alkenyl residue with between 3 and 4 C-atoms
and R3 is a branched or unbranched alkyl residue with between 1 and 5 C-atoms,
except for
2,6-dimethyl-3-(1-methylethenyl)-tetrahydropyran (CAS-Nr 1008981-43-8):

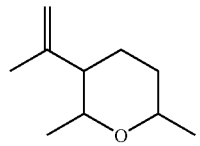

6-methyl-3-(1-methylethenyl)-2-(2-methylpropyl)-tetrahydropyran (CAS-Nr 1005159-81-8):

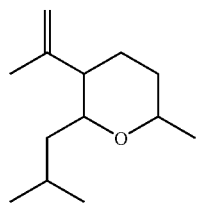

2-methyl-3-n-propyl-tetrahydropyran (CAS-Nr 13687-01-9):

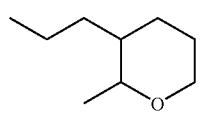

and 2-methyl-3-n-butyl-tetrahydropyran (CAS-Nr 13687-02-0):

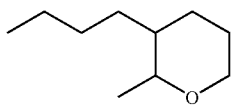

Alkylated tetrahydropyran derivates are described as sensorially active substances inter alia for example in Perfumer & Flavorist, Vol 17, 1992, 77-92 and in PAFAI Journal (1984), 6(3), 15-18.

From this structure class above all rose oxide [2-(2-methyl-1-propenyl)-4-methyltetrahydropyran, CAS-Nr 16409-43-1; FEMA-Nr 3236] and limetol (2-vinyl-2,6,6-trimethyltetrahydropyran, CAS-Nr 7392-19-0; FEMA-Nr 3735) are used as flavoring substances; for limetol for example as described in U.S. Pat. No. 5,137,741. For both substances a taste enhancing effect in flavors is demonstrated: for limetol U.S. Pat. No. 5,589,158 describes a taste enhancing effect for mint flavors in combination with neryl acetate and benzyl benzoate; for rose oxide a taste modulating effect in cask-conditioned drinks is described in DE 698 24 198 T2. Both rose oxide and limetol, however, have a noticeable characteristic taste profile, which restricts or even prevents them being used as taste modulating substances in certain areas of application.

In the oral hygiene area, taste modulating substances are known; thus in DE 102 25 350 A1 the alkylated 1,3-dioxanes are described as flavoring substances, with freshness-intensifying and flavor-intensifying characteristics. A disadvantage of this class of compound, however, is the limited stability in various media such as for example toothpaste.

The acyclic ethers described in WO 02/41861 A1 also have flavor-intensifying characteristics. Unlike the cyclical ethers described here, however, their effect does not begin immediately but with a certain time delay. The advantage of all the cyclical ethers according to the invention, on the other hand, lies in the immediacy of their effect (boost effect).

Within the group of compounds according to the invention and of mixtures comprising or containing two, three, four or more compounds, certain alkylated tetrahydropyrans are preferred. Particular preference is for the compound or one of the compounds to be selected from those alkylated tetrahydropyrans of formula (I), in which each R1 independently of the other is a methyl, ethyl or vinyl residue, R2 is an isopropyl, isopropenyl, sec-butyl or sec-butenyl residue, and R3 is an unbranched alkyl residue with between 1 and 3 C-atoms.

Here the compound or at least one of the compounds in the mixture is preferably an alkylated tetrahydropyran of this type, in which each R1 independently of the others is a methyl or ethyl residue, R2 is an isopropyl or sec-butyl residue and R3 is a methyl or ethyl residue.

The compound or one of the compounds in the mixture is preferably selected from the group comprising 2,6-diethyl-5-isopropyl-2-methyl-tetrahydropyran, 6-ethyl-5-isopropenyl-2-methyl-2-vinyltetrahydropyran, 2,6-dimethyl-5-isopropyl-2-ethyltetrahydropyran, 2,6-dimethyl-5-isopropenyl-2-vinyltetrahydropyran, 2,6-diethyl-5-sec.-butyl-2-methyl-tetrahydropyran and 2,6-dimethyl-5-sec.-butyl-2-ethyltetrahydropyran.

A quite particularly preferred compound for achieving the object of the invention is 2,6-diethyl-5-isopropyl-2-methyltetrahydropyran; corresponding preference is also for mixtures according to the invention containing this compound.

The invention is based on the surprising finding that alkylated tetrahydropyrans according to the invention rapidly and perceptibly intensify the freshening effect of flavor compositions (compositions containing one or more flavoring substance(s) and/or flavorings) with a freshening effect, but without exhibiting a strong characteristic taste.

The mixtures according to the invention comprise two, three, four or more compounds of formula (I), preferably in each case in one of the embodiments indicated above as preferred. It is also preferred if in a mixture to be used according to the invention not only a compound of formula (I) indicated above as being particularly preferred is present, i.e. not just one compound which comprises one, a plurality of or exclusively particularly preferred groups R1, R2 and R3, but two or more particularly preferred compounds of formula (I) according to the invention. Preferably, therefore, two, three or all compounds in a mixture according to the invention comprising compounds of formula (I) are selected from the group of compounds indicated as preferred.

The compounds of formula (I) can be obtained using manufacturing methods known to a person skilled in the art. For example, compounds of formula (I) can be manufactured in a method as illustrated in the following diagram. The conversion of the aldehyde (B) with the alcohol component (A) leads to the corresponding cyclized tetrahydropyran compound (C), to be subsumed under formula (I). Tetrahydropyran compound (C) can optionally be reduced in a second reaction step to the tetrahydropyran compound (D), likewise to be subsumed under formula (I).

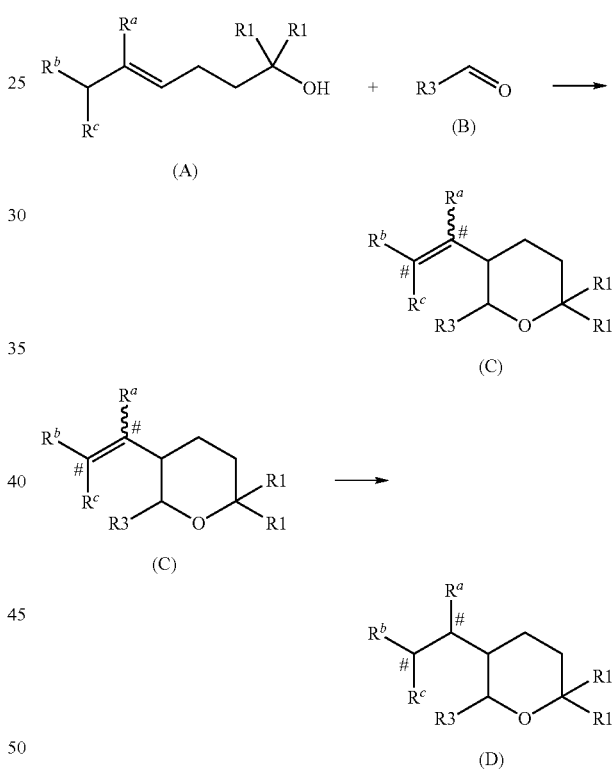

in which

R1 and R3 in each case have the abovementioned (if necessary preferred) meaning, and $R^a$, $R^b$ and $R^c$ independently of one another represent hydrogen, methyl or ethyl, on condition that $R^a$, $R^b$ and $R^c$ in total contain 1 or 2 C-atoms, i.e. that the residues $R^a$, $R^b$ and $R^c$ together with the two CH-residues marked with # correspond in total to the residue $R^2$ in formula (I).

The conversion of alcohol (A) with aldehyde (B) preferably takes place in the presence of acid catalysts. Examples of acid catalysts that can be used are for example inorganic acids such as phosphoric acid, polyphosphoric acid, hydrochloric acid, nitric acid, sulfuric acid, organic acids such as methane sulfonic acid, toluene sulfonic acid or trifluoroacetic acid.

Additionally solid acids such as acid ion exchangers, acid aluminosilicate or acid zeolites can be used.

Further preferred acid catalysts are Lewis acids such as for example $AlX_3$, $ZnX_2$, $FeX_3$, $TiX_4$, in which X stands for a halide from the group chlorine, bromine or iodine, and $BF_3$, in particular $AlCl_3$, $ZnCl_2$, $FeCl_3$, $TiCl_4$ and $BF_3$ adducts.

Particularly preferred catalysts are sulfuric acid, phosphoric acid and $BF_3$ adducts, in particular $BF_3$ etherate.

The molar ratio of alcohol (A) to aldehyde (B) is preferably in the range between 1:5 and 1:3, particularly preferably in the range between 1:3 and 1:1. Particular preference is for a molar ratio of alcohol (A) to aldehyde (B) of 1 to 1.05-1.2 (i.e. a slight excess of aldehyde).

The reaction temperature is preferably in the range between −20° C. and 50° C., preferably in the range between −10° C. and 40° C. and particularly preferably in the range between 0° C. and 15° C.

In the conversion of (A) with (B) the following temperature profile is particularly preferred: initially the reaction of the alcohol component (A) with the aldehyde component (B) takes place cold (preferably at 0-10° C.). In the event of catalysis with a protonic acid, heating of the reaction mixture to approximately 60-80° C. preferably then follows, in order to achieve the most complete conversion possible. Such subsequent heating can be dispensed with, however, in the event of catalysis with a Lewis acid.

Compounds of formula (D), here in particular those compounds of formula (I), which do not have any C—C double bonds can be obtained by means of reduction from the corresponding unsaturated compounds of formula (C), preferably by means of hydrogenation on hydrogenation catalysts in a hydrogen atmosphere.

Examples of suitable hydrogenation catalysts for reducing the C—C double bond(s) present in formula (C) are elements of 8th subgroup of the periodic table. Particularly advantageous here are the elements nickel, palladium, platinum, rhodium, iridium, ruthenium and mixtures, compounds and alloys of these. These catalysts, preferably in elementary and finely distributed form, can be used applied to carriers or together with other metals or their compounds. Advantageous carrier materials that can be mentioned are activated charcoal, aluminum oxides, metal oxides, silica gels, zeolites, clays, granulated clays, amorphous aluminum silicates, or other inorganic or polymeric carriers.

The hydrogen pressure during the hydrogenation reaction is in the range between 1 and 200 bar, preferably in the range between 1 and 100 bar, particularly preferably in the range between 5 and 50 bar.

Compounds of formula (I) can be purified according to normal methods, e.g. by distillation.

In order to achieve fresh, etheric, minty, cooling, sweet and fruity taste notes in combination with a fresh relieving feeling in the mouth, pharyngeal cavity and the respiratory tract the tetrahydropyrans according to the invention in pure form, can be combined with one another or in a particularly preferred form with flavoring substances and/or flavors.

Preference is therefore also for mixtures containing or comprising
  a) one, two, three, four or more alkylated tetrahydropyrans according to the invention;
  b) one or more (volatile) flavoring substance and/or flavors, in particular one or more substance(s) selected from the group comprising substances with a physiological cooling action, flavoring substances without a physiological cooling action, substances with a trigeminal or mouthwatering effect without a physiological cooling action and flavor-modulating substances;
  c) and optionally a cosmetically or pharmaceutically acceptable carrier.

The term flavoring substance(s) is used in the present invention in the strictest sense of the Council Directive 88/388/EEC of Jun. 22, 1988, published in OJ L 184 of Jul. 15, 1988, page 61. According to this Directive flavoring substance means:

"a defined chemical substance with flavouring properties which is obtained by:
  (i) appropriate physical processes (including distillation and solvent extraction) or enzymatic or microbiological processes from material of vegetable or animal origin either in the raw state or after processing for human consumption by traditional food-preparation processes (including drying, torrefaction and fermentation),
  (ii) chemical synthesis or isolated by chemical processes and which is chemically identical to a substance naturally present in material of vegetable or animal origin as described in (i),
  (iii) chemical synthesis but which is not chemically identical to a substance naturally present in material of vegetable or animal origin as described in (i)"

Examples of flavoring substances to be used according to the invention are listed in sections 1 to 3 of Commission Decision 1999/217/EC of Feb. 23, 1999 adopting a register of flavouring substances used in or on foodstuffs drawn up in application of Regulation 2232/96/EC of the European Parliament and of the Council of Oct. 28, 1996 (1999/217/EC), which can be consulted in the Official Journal of the European Communities L 84/1 of Mar. 27, 1999 and in the Annex to Commission Decision of Jul. 18, 2000 amending Decision 1999/217/EC adopting a register of flavouring substances used in or on foodstuffs. (2000/489/EC), which can be consulted in the Official Journal of the European Communities L 197/53 of Aug. 3, 2000.

A volatile flavoring substance in the context of the present invention is preferably understood to be a sensorially active component with a vapor pressure of greater than or equal to 0.01 Pa at 25° C., in particular with a vapor pressure of greater than or equal to 0.025 Pa at 25° C. Most volatile flavoring substances have a vapor pressure of greater than or equal to 1 Pa at 25° C., so that such substances especially can be considered to be flavoring substances within the meaning of the present invention.

In the following in particular the term "cooling substance" will be used to designate cooling substances with a physiological effect (cooling active substances). Cooling substances are regularly used in order to bring about a cooling sensorial impression on the skin or the mucous membrane, for example on the mucous membrane in the oral, nasal and/or pharyngeal cavity, but in which no physical cooling actually takes place as for example in the evaporation of solvents. Both individual components and mixtures can be used as cooling substances. The most well-known cooling substance is L-menthol.

Suitable further flavoring substances—with or without a physiological cooling action—are both complex natural raw materials and plant extracts and essential oils, or fractions and homogeneous substances produced from these and also homogeneous synthetically or biotechnologically produced flavoring substances.

Examples of natural raw materials are peppermint oils, spearmint oils, mentha arvensis oils, aniseed oils, clove oils, citrus oils, cinnamon bark oils, winter green oils, cassia oils, davana oils, spruce needle oils, eucalyptus oils, fennel oils, galbanum oils, ginger oils, chamomile oils, cumin oils, rose oils, geranium oils, sage oils, parsley oils, yarrow oils, star anise oils, thyme oils, juniper berry oils, rosemary oils, angelica root oils, and fractions of these oils.

Examples of homogeneous flavoring substances are anethole, menthol, menthone, isomenthone, methyl acetate, menthofuran, mint lactone, eucalyptol, limonene, eugenol, pinene, sabinene hydrate, 3-octanol, carvone, gamma-octalactone, gamma-nonalactone, germacrene-D, viridiflorol, 1,3E,5Z-undecatriene, isopulegol, piperitone, 2-butanone, ethyl formate, 3-octyl acetate, isoamyl isovalerate, isoamyl acteate, isoamyl butyrate, ethyl butyrate, vanillin, ethyl vanillin, hexanol, hexanal, cis-3-hexenol, cis-3-hexenyl acetate linalool, alpha-terpineol, cis and trans carvyl acetate, p-cymol, damascenon, damascone, rose oxide, dimethyl sulfide, fenchol, acetaldehyde diethyl acetal, cis-4-heptenal, isobutyraldehyde, isovaleraldehyde, cis-jasmone, anisaldehyde, methyl salicylate, myrtenyl acetate, 2-phenylethyl alcohol, 2-phenylethyl isobutyrate, 2-phenylethyl isovalerate, cinnamaldehyde, geraniol, nerol. In the case of chiral compounds, the flavoring substances can be present as racemate or an individual enantiomer or as enantiomer-enriched mixture.

Examples of other flavoring substances or flavors which can be advantageously combined with the tetrahydropyrans according to the invention are substances having a physiologically cooling action, that is to say substances which cause an impression of cold in the mucous membranes. Such substances having a cooling action are, in particular, I-menthol, 1-isopulegol, menthone acetals (for example menthone glycerin acetal), menthyl esters, esters of menthol and hydroxycarboxylic acids with between 2 and 6 C-atoms (for example menthyl lactate), substituted menthane-3-carboxamides (for example N-ethylmenthane-3-carboxamide), branched alkane carboxylic acid amides (for example 2-isopropyl-N,2,3-trimethylbutanamide), 3,3,5-trimethyl cyclohexanol, 3-menthoxy-1,2-propandiol, 3-menthoxy-2-methyl-1,2-propandiol, 2-menthoxyethanol, 2-menthoxypropanol, 3-menthoxypropanol, 4-menthoxybutanol, 2-hydroxyethyl menthyl carbonate, 2-hydroxypropyl menthyl carbonate, glycerin menthyl carbonate, N-acetyl glycine menthyl ester, menthylhydroxycarboxyclic acid esters (for example menthyl 3-hydroxybutyrate), menthane-3,8-diol, menthyl-2-methoxyacetate, menthyl 2-(2-methoxyethoxy)acetate, menthyl monosuccinate, 2-mercapto-cyclodecanone, menthyl 2-pyrrolidin-5-one carboxylate.

Further examples of substances with a physiological cooling action, that is to say substances which cause an impression of cold in the mucous membranes, which can be advantageously combined with the tetrahydropyrans according to the invention, are shown in a summary table in WO 2008/138162 A1. Of these particular preference is for aromatic menthane carboxylic acid amides. Such as for example WS-12 [N-(4-methoxyphenyl)-menthane carboxylic acid amide] and Evercool 180 [N-(4-cyanomethylphenyl)-p-menthane carboxamide], and (1R,2S,5R)-2-isopropyl-5-methyl-N-(2-(pyridin-2-yl)ethyl)cyclohexane carboxamide.

Preferred substances with a physiological cooling action are menthyl esters, menthone acetals, menthane-3-carboxylic acid amides and branched alkane carboxylic acid amides.

Further preferred substances with a physiological cooling action are menthyl oxamate, menthyl N-methyl oxamate, menthyl N,N-dimethyloxamate, menthyl N-ethyloxamate, menthyl N,N-diethyloxamate, menthyl N-propyloxamate, menthyl N,N-dipropyloxamate, menthyl N-isopropyloxamate, menthyl N,N-diisopropyloxamate, menthyl N-cyclo-propyloxamate, menthyl N-butyloxamate, morpholin-4-yl-oxoacetic acid-(1R,2S,5R)-2-isopropyl-5-methyl-cyclohexyl ester, menthyl N-(2-methoxyethyl)-oxamate, menthyl N-(3-methoxypropyl)-oxamate, menthyl N-(2-hydroxyethyl)-oxamate, menthyl N-(3-hydroxypropyl)-oxamate.

In mixtures according to the invention one or more flavoring substances without a physiological cooling action are selected from the group comprising substances which bring about a spicy hot taste or a sensation of hotness or heat on the skin and mucous membranes or prickling or tingling sensation in the oral cavity and pharyngeal cavity, in particular paprika powder, chili pepper powder, paprika extracts, pepper extracts, chili pepper extracts, ginger root extracts, extracts from grains of paradise (Aframomum melegueta), paracress extracts (Jambu oleoresin; Spilanthes acmella, or Spilanthes oleracea), Japanese pepper extracts (Zanthoxylum piperitum), Kaempferia galanga extracts, Alpinia galanga extracts, water pepper extracts (Polygonium hydropiper), capsaicin, dihydrocapsaicin, gingerol, paradol, shogaol, piperine, sanshool I, sanshool II, sanshoamide, spilanthol, carboxylic acid N-vanillylamides, in particular nonanbic acid N-vanillylamide, 2-nonenoic acid amides, in particular 2-nonenodic acid N-isobutylamide, 2-nonenoic acid N-4-hydroxy-3-methoxyphenylamide, 2,4-decadienic acid amides, preferably 2,4-decadienic acid N-isobutyl amides, in particular pellitorines in accordance with WO 2004/000787 or US 2004/0241312, in particular 2E,4Z-decadienic acid-N-isobutylamide (cis-pellitorine) and 2E,4E-decadienic acid-N-isobutylamide (trans-pellitorine) and mixtures of these, alkene carboxylic acid-N-alkamides according to DE 103 51 422, alkyl ethers of 4-hydroxy-3-methoxybenzyl alcohol, in particular 4-hydroxy-3-methoxybenzyl n-butyl ether, alkyl ethers of 3-hydroxy-4-methoxybenzyl alcohol, alkyl ethers of 3,4-dimethoxybenzyl alcohol, alkyl ethers of 3-ethoxy-4-hydroxybenzyl alcohol, alkyl ethers of 3,4-methylenedioxybenzyl alcohol, acetals of vanillin, acetals of ethylvanillin, acetals of isovanillin, (4-hydroxy-3-methoxyphenyl)acetamides, in particular (4-hydroxy-3-methoxyphenyl)acetic acid N-n-octyl amide, allyl isothiocyanate, nicotinaldehyde, methyl nicotinate, propyl nicotinate, 2-butoxyethyl nicotinate, benzyl nicotinate and 1-acetoxychavicol.

In flavoring compositions the total quantity used of the alkylated tetrahydropyrans according to the invention is preferably between 0.5 and 30% by weight, preferably between 1 and 20% by weight and particularly preferably between 2 and 10% by weight, with reference to the total weight of the flavoring composition.

The invention also indicates a preparation used for nutrition, oral hygiene or pleasure or a pharmaceutical or cosmetic preparation, comprising (i) one or more alkylated tetrahydropyrans according to the invention or (ii) a mixture according to the invention, wherein component (i) or, if present, (ii) is present in a sufficient concentration
    to achieve a physiological cooling action on the skin and/or a mucous membrane and/or
    to convey, modify or intensify a feeling of freshness in the mouth, throat and/or respiratory tract.

The alkylated tetrahydropyrans according to the invention are present (preferably as a component in the flavoring compositions in the quantity ranges indicated above), according to the type of preparation, generally in such preparations preferably in a total proportion of between 10 ppm and 2% by weight. Preference is for a content of between 25 ppm and 1% by weight; particular preference is for a content of between 50 ppm and 0.5% by weight, with greatest preference for a content of between 100 ppm and 0.25% by weight, in each case with respect to the total preparation. For certain particularly preferred preparations, in particular oral hygiene products, in the following preferred contents are given.

The flavoring substances or flavor compositions containing the compounds according to the invention can be used in pure form, as solutions or also in a special preparation form and incorporated in ready to use products.

Suitable solvents are for example ethyl alcohol, 1,2-propylene glycol, glycerin, triacetin, benzyl alcohol and fatty oils such as for example coconut oil or sunflower oil.

The preparations containing the compounds according to the invention can also contain additives and inactive ingredients, in particular preservatives, colorings, antioxidants, flow agents, thickening agents, etc.

The compounds according to the invention can be bonded to a carrier, spray-dried or encapsulated. In the bonded form compounds according to the invention can be bonded to or in a carrier, for example cooking salt, sugar, starches or molten sugar. The spray-dried form is manufactured from the liquid compositions by producing an emulsion with the addition of defined quantities of a carrier substance, preferably biopolymers such as starch, modified starches, maltodextrin and gum Arabic. This emulsion is dried in spray driers by fine distribution and simultaneous heat application. The result is a powder with the desired loading of liquid composition. The encapsulated form is likewise manufactured from the liquid compositions with the addition of a carrier substance. There are various technologies with which capsules can be manufactured. The most common are extrusion, spray granulation and coacervation. The particle sizes normally range between 10 μm and 5 mm. The most common capsule materials are various starches, maltodextrin and gelatin. The liquid or solid flavoring substance or flavor compositions are incorporated in these capsules and can be released by various mechanisms such as application of heat, pH shift or chewing pressure.

The preparations containing the compounds according to the invention can advantageously be used above all in oral hygiene products such as toothpastes and mouthwashes, chewing gums, foodstuffs, such as confectionery and hard candies, luxury items such as tobacco and pharmaceutical preparations and nasal sprays.

The total content of a flavor composition containing one or more compounds according to the invention is in ready to use mouthwashes preferably between 0.01 and 1% by weight, preferably between 0.05 and 0.5% by weight, with particular preference for a content of between 0.1 and 0.3% by weight, in each case with respect to the mouthwash in total.

In mouthwash concentrates the total content of the flavor composition containing one or more compounds according to the invention is preferably between 0.1 and 15% by weight, with preference for a content of between 0.5 and 8% by weight, and particular preference for between 1 and 5% by weight, in each case with respect to the mouthwash concentrate in total.

In toothpastes the total content of the flavor composition containing one or more of the compounds according to the invention is preferably between 0.1 and 5% by weight, with preference for between 0.5 and 2% by weight, and particular preference for between 0.8 and 1.5% by weight, in each case with respect to the toothpaste in total.

In chewing gums the total content of the flavor composition containing one or more of the compounds according to the invention is preferably between 0.1 and 5% by weight, with preference for between 0.5 and 3 by weight, and particular preference for between 0.8 and 2.5% by weight, in each case with respect to the chewing gum in total.

In hard candies the total content of the flavor composition containing one or more of the compounds according to the invention is preferably between 0.01 and 2% by weight, with preference for between 0.05 and 1% by weight, and particular preference for between 0.1 and 0.5% by weight, in each case with respect to the hard candy in total.

The preparation according to the invention is preferably (i) a preparation for nutrition or pleasure selected from baked goods, confectionery, alcoholic or non-alcoholic drinks, instant drinks, meat products, eggs or egg products, cereal products, milk products, fruit preparations, vegetable preparations, snack items, fat- and oil-based products or emulsions of these, other convenience foods and soups, spices, spice mixes, seasonings, semi-finished goods, food supplements; or (ii) a preparation for oral hygiene, preferably with a dental care agent basis, and selected from the groups comprising: toothpaste, tooth crème, tooth gel, tooth powder, tooth cleaning fluid, tooth cleaning foam, mouthwash, tooth crème and mouthwash as a 2-in-1 product, hard candy, mouth spray, dental floss and dental care chewing gum; or (iii) a pharmaceutical preparation, wherein the preparation is preferably an oral pharmaceutical preparation or a nasally applied preparation, preferably in the form of capsules, tablets, sugar-coated pills, granulates, pellets, solid mixtures, dispersions in liquid phases, as emulsions, as powders, as solutions, as pastes or as other preparations to be swallowed or chewed; or (iv) a cosmetic preparation, selected from the group comprising: soap, syndet, liquid wash, shower or bath preparation, emulsion, ointment, paste, gel, oil, toner, balsam, serum, powder, eau de toilette, toilette, eau de Cologne, perfume, wax, stick, roll-on, (pump-)spray, aerosol (foaming, non-foaming or after-foaming), foot care product, beard shampoo or care preparation, insect repellent, sunscreen preparation, aftersun preparation, shaving preparation, aftershave, depilatory product, hair care product, conditioner, hair tonic, hair lotion, hair rinse, hair cream, pomade, permanent wave and setting lotion, hair smoothing product, hair strengthener, styling aid, blonding product, hair lightener, hair conditioner, hair mousse, hair toning product, nail care product, deodorant, antiperspirant, mouthwash, oral douche, make-up, make-up remover, eye care cream, lip cosmetics, lip care preparation, decorative cosmetics, bath product or face mask.

Oral hygiene products, in particular toothpastes, which are flavored with the compositions containing the compounds according to the invention generally comprise an abrasive system (abrasive or polishing agent), such as for example silicas, calcium carbonates, calcium phosphates, aluminum oxides and/or hydroxyapatites, surface-active substances such as for example sodium lauryl sulfate, sodium lauryl sarcosinate and/or cocamidopropyl betaine, humectants such as for example glycerol and/or sorbitol, thickeners, such as for example carboxymethyl cellulose, polyethylene glycols, carrageenan and/or Laponite®, sweeteners such as for example saccharin, cooling active agents, stabilizers and active ingredients, such as for example sodium fluoride, sodium monofluorophosphate, tin difluoride, quaternary ammonium fluorides, zinc citrate, zinc sulfate, tin pyrophosphate, tin dichloride, blends of different pyrophosphates, triclosan, cetylpyridinium chloride, aluminum lactate, potassium citrate, potassium nitrate, potassium chloride, strontium chloride, hydrogen peroxide and/or sodium bicarbonate.

Chewing gums which are flavored with the compositions containing the compounds according to the invention, generally comprise a chewing gum base, i.e. a chewable mass which becomes plastic on chewing, sugars of various kinds, sugar substitutes, other sweet-tasting substances, sugar alcohols (in particular sorbitol, xylitol, mannitol), cooling active agents, taste-correcting agents for unpleasant taste impressions, other taste modulators for further, generally not unpleasant taste impressions, taste-modulating substances (for example inositol phosphate, nucleotides such as guanosine monophosphate, adenosine monophosphate or other substances such as sodium glutamate or 2-phenoxypropionic acid), humectants, thickeners, emulsifiers and stabilizers.

In the prior art, numerous different chewing gum bases are known, wherein is it necessary to distinguish between "chewing gum" or "bubble gum" bases, wherein the latter are softer, so that chewing gum bubbles may also be formed therewith. These days, in addition to traditionally used natural resins or the natural latex chicle, common chewing-gum bases usually comprise elastomers such as polyvinyl acetates (PVA), polyethylenes, (low or medium molecular weight) polyisobutenes (PIB), polybutadienes, isobutene/isoprene copolymers (butyl rubber), polyvinyl ethyl ether (PVE), polyvinyl butyl ether, copolymers of vinyl esters and vinyl ethers, styrene/butadiene copolymers (styrene/butadiene rubber, SBR), or vinyl elastomers, for example based on vinyl acetate/vinyl laurate, vinyl acetate/vinyl stearate or ethylene/vinyl acetate, and mixtures of the above-stated elastomers, as described for example in EP 0 242 325, U.S. Pat. No. 4,518,615, U.S. Pat. No. 5,093,136, U.S. Pat. No. 5,266,336, U.S. Pat. No. 5,601,858 or U.S. Pat. No. 6,986,709. In addition, chewing gum bases comprise further constituents such as for example (mineral) fillers, plasticizers, emulsifiers, antioxidants, waxes, fats or fatty oils, such as for example hardened (hydrogenated) plant or animal fats, mono-, di- or triglycerides. Suitable (mineral) fillers are for example calcium carbonate, titanium dioxide, silicon dioxide, talcum, aluminum oxide, dicalcium phosphate, tricalcium phosphate, magnesium hydroxide and mixtures thereof. Suitable plasticizers or agents for preventing adhesion (detackifiers) are for example lanolin, stearic acid, sodium stearate, ethyl acetate, diacetin (glycerol diacetate), triacetin (glycerol triacetate), triethyl citrate. Suitable waxes are for example paraffin waxes, candelilla wax, carnauba wax, microcrystalline waxes and polyethylene waxes. Suitable emulsifiers are for example phosphatides such as lecithin, mono- and diglycerides of fatty acids, for example glycerol monostearate.

In the application of finished products which contain the composition with the compounds according to the invention, it transpires that the compounds according to the invention or the compositions containing the compounds according to the invention are particularly well-suited to freshening breathing air and neutralizing or reducing bad breath.

The use of the compounds according to the invention or the mixtures containing the compounds according to the invention in oral care products (oral hygiene products), such as for example mouthwashes and toothpastes, and chewing gums, means that unpleasant, above all bitter or metallic taste impressions are to some extent masked or neutralized, which are for example caused by substances such as triclosan, zinc citrate, zinc sulfate, poly- and pyrophosphates, bicarbonate, strontium- and potassium salts, tin pyrophosphate, and chloride, aluminum lactate, hydrogen peroxide, fluoride, vitamins, cetylpyridinium chloride and emulsifiers such as for example in particular sodium lauryl sulfate, sodium lauryl sarcosinate and cocamidopropylbetaine, and sweeteners such as for example aspartame, saccharin, Acesulfame-K, sorbitol; xylitol, cyclamate (for example sodium cyclamate), sucralose, alitame, neotame, thaumatine, neohesperidin dihydrochalcone, matitol, lactitol or chewing gum masses.

A further positive characteristic of the compounds according to the invention that can be highlighted is their stability in toothpastes with a chalk or bicarbonate basis which are difficult to flavor because of their alkaline pH value.

The compounds according to the invention or the compositions containing the compounds according to the invention are, however, also suitable for use in pharmaceutical preparations such as for example nasal drops and sprays or rub-in preparations. In particular the compositions containing the compounds according to the invention are suitable for masking the bitter taste of medicines.

Further aspects of the present invention are apparent from the following examples and the attached claims. Unless otherwise stated, all data relate to weight.

In some examples a pellitorine solution (hereinafter referred to as "pellitorine solution PLM") was used containing 10% pellitorine (comprising 4.9% 2E,4Z-decadienic acid N-isobutylamide and 94.3% 2E,4E-decadienic acid N-isobutylamide), 45% propylene glycol and 45% natural peppermint oil (Mentha arvensis).

BRIEF DESCRIPTION OF THE DRAWING(S)

FIG. 1 shows a spider diagram comparing two toothpaste samples.

EXAMPLES

Example 1.0

Panel Investigation of a Toothpaste Sample (13 Sensorially Trained Test Subjects)

Two toothpaste samples [toothpaste formulation I from Example 2.15 ("silica opaque"), flavor from Example 2.1 ("peppermint type")] were compared with one another. The test subjects were asked to clean their teeth for one minute and then to sensorially assess the samples. The descriptors shown in the spider diagram below were sought (scale from 0 (=does not correspond to the descriptor) to 8 (corresponds very strongly with the descriptor)).

One sample contained the "peppermint type" flavor without compounds according to the invention (dosing 0.9%; shaded area of FIG. 1) and the comparative sample contained the flavor from Example 2.1 (dosing 0.8%; line drawn through Diagram 1) with the compounds according to the invention.

Thus the compounds do not affect the taste profile of the flavor; rather they intensify the taste impression of this in the desired manner. The impression of freshness and fullness is intensified and the overall effect of the flavor develops better. In the initial phase of brushing in particular (when the paste foams) the taste impression is intensified significantly ("Freshness during" (freshness during brushing) and "Impact" (overall taste impression 10 seconds after cleaning) descriptors). Out of 13 test subjects 9 preferred the samples which contained the compounds according to the invention (see FIG. 1).

| Descriptor | Meaning |
| --- | --- |
| "Peppermint" | Peppermint taste impression |
| "Menthol" | Menthol taste impression |
| "Impact" | Overall taste impression 10 seconds after brushing |
| "Freshness during" | Freshness impression during brushing |
| "Fullness" | Fullness of the flavor |
| "Sweetness" | Sweetness of the flavor |
| "Strength" | Strength of the flavor |
| "Sharpness" | Sharpness of the flavor |
| "Cooling" | Impression of coolness |

| Descriptor | Meaning |
| --- | --- |
| "Freshness after" | Impression of freshness after brushing |
| "Long Lasting Taste" | Lingering of taste/length of taste impression |

Example 1.1

Manufacture of Various alkyl- and alkenyl-substituted tetrahydropyrans Using the Example of 2,6-diethyl-5-isopropyl-2-methyl-tetrahydropyran Stage 1:

46 g of water were placed in a 2 liter double-walled reactor with thermometer and dropping funnel and 346 g phosphoric acid (85%) were added (thus diluted to 75% concentration) followed by cooling to 0° C. 116.2 g propion aldehyde were mixed with 308.5 g linalool and droppered in for approximately 1 hour with vigorous stirring at up to an internal temperature of 5° C. Once addition was complete the formulation was stirred for a further 4 hours at between 0° C. and 5° C., and then heated to room temperature (approximately 20° C.). To allow full conversion it was then heated for approximately 20 minutes at 70° C. At 65-70° C. the phases were separated. The organic phase was washed twice with 100 g water on each occasion and then the raw formulation was distilled via a 30 cm packed column. 251 g product with a content of 84% of 6-ethyl-5-isopropenyl-2-methyl-2-vinyltetrahydropyran were obtained (54% of theoretical yield).

Stage 2:

The hydrogenation was carried out in a hydrogenation autoclave. 202 g of 6-ethyl-5-isopropenyl-2-methyl-2-vinyltetrahydropyran (from stage 1) were filled along with 8 g of Pd/active charcoal (Pd content: 5%) in the autoclave in the autoclave and hydrogenated at 30 bar hydrogen pressure. The reaction took place exothermically from 20° C. to approximately 50° C., after which heating to 90° C. was carried out. The $H_2$ absorption was complete after 35 minutes. 107% of theoretical $H_2$ was absorbed. The catalyst was filtered off and this was then rinsed with ethanol. The material obtained in this way was distilled via a 120 cm column. 131 g of 2,6-diethyl-5-isopropyl-2-methyl-tetrahydropyran (purity >97%) were obtained (73% of theoretical yield).

6-ethyl-5-isopropenyl-2-methyl-2-vinyltetrahydropyran

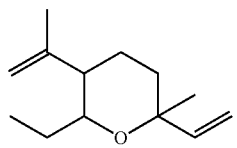

$^1$H-NMR (Blend of isomers, 400 MHz, $CDCl_3$): δ=0.92 (t, J=7.4 Hz, 3H), 1.18-1.31 (m, 2H), 1.19 (s, 0.5×3H), 1.28 (s, 0.5×3H), 1.45-1.95 (m, 6 H), 1.62 (dd, J=0.9 Hz, J=1.5 Hz, 0.5×3H), 1.70 (dd, J=1.0 Hz, J=1.4 Hz, 0.5×3H), 3.45 (ddd, J=2.6 Hz, J=8.7 Hz, J=10.2 Hz, 0.5×1H), 3.53 (ddd, J=2.6 Hz, J=8.2 Hz, J=9.7 Hz, 0.5×1H), 4.68-4.76 (m, 1H), 4.89-5.25 (m, 1H), 5.79 (ddd, J=1.0 Hz, J=11.1 Hz, J=17.8 Hz, 1 H), 5.91 (dd, J=10.9 Hz, J=17.4 Hz, 1H) ppm.

$^{13}$C-NMR (Blend of isomers, 100 MHz, $CDCl_3$): δ=10.18 ($CH_3$), 10.33 ($CH_3$), 20.26 ($CH_3$), 20.39 ($CH_3$), 21.03 ($CH_3$), 27.28 ($CH_2$), 27.44 ($CH_2$), 27.60 ($CH_2$), 27.96 ($CH_2$), 27.99 ($CH_2$), 31.55 ($CH_3$), 35.52 ($CH_2$), 35.92 ($CH_2$), 50.87 (CH), 50.96 (CH), 74.38 (C), 74.69 (CH), 76.04 (C), 76.17 (CH), 111.04 ($CH_2$), 112.17 ($CH_2$), 112.21 ($CH_2$), 115.34 ($CH_2$), 144.42 (CH), 147.77 (CH), 148.69 (C) ppm.

MS: m/z (%)=194 (1) [M⁻], 136 (10), 121 (19), 107 (14), 93 (32), 81 (11), 68 (100), 53 (8).

2,6-diethyl-5-isopropyl-2-methyl-tetrahydropyran

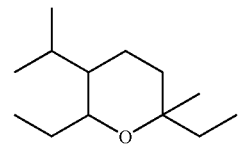

$^1$H-NMR (Blend of isomers, 400 MHz, $CDCl_3$): δ=0.74-0.96 (m, 12H), 1.09 (s, 0.5×3H), 1.10 (s, 0.5×3H), 1.10-1.72 (m, 8H), 1.81-1.93 (m, 2 H), 3.22 (ddd, J=1.0 Hz, J=2.7 Hz, J=8.4 Hz, 0.5×1H), 3.33 (ddd, J=2.8 Hz, J=8.2 Hz, J=10.1 Hz, 0.5×1H) ppm.

$^{13}$C-NMR (Blend of isomers, 100 MHz, $CDCl_3$): δ=7.38 ($CH_3$), 7.72 ($CH_3$), 9.59 ($CH_3$), 9.87 ($CH_3$), 15.86 ($CH_3$), 15.88 ($CH_3$), 18.07 ($CH_2$), 18.32 ($CH_2$), 19.39 ($CH_3$), 21.33 ($CH_3$), 25.66 ($CH_2$), 25.78 ($CH_2$), 25.84 ($CH_2$), 26.86 (CH), 26.87 (CH), 27.66 ($CH_3$), 34.89 ($CH_2$), 36.19 ($CH_2$), 37.17 ($CH_2$), 44.70 (CH), 45.13 (CH), 72.50 (C), 72.51 (C), 72.83 (CH), 73.03 (CH) ppm.

MS: m/z (%)=198 (1) [M⁺], 169 (66), 151 (79), 111 (25), 109 (21), 95 (48), 83 (18), 70 (100), 55 (57).

Example 1.2

Manufacture of Various alkyl- and alkenyl-Substituted tetrahydropyrans Using the Example of 2,2,6-trimethyl-5-isopropyltetrahydropyran 42 g of acetaldehyde in 600 ml diethylether were placed in a 2 liter three-necked flask and cooled to 0° C. 140 g of a 48% solution of boron trifluoride diethyl etherate were then added and stirred for 10 minutes at 0° C. 124 g of 2,6-dimethyl-hept-5-en-2-ol dissolved in 100 ml diethyl ether were droppered into the reaction solution at 0° C. Once addition was complete stirring continued for a further hour at 0° C. followed by heating to room temperature. Once the reaction solution had been stirred for 12 hours at room temperature, quenching was carried out with saturated ammonium chloride solution (500 ml) and following conditioning of the raw product obtained distillation was performed via a 30 cm packed column. 82 g of 2,2,6-trimethyl-5-isopropenyltetrahydropyran with a purity of 98% were obtained (55% of theoretical yield).

A yield of 85% for the 2,2,6-trimethyl-5-isopropyltetrahydropyran was obtained by hydrogenation (similar to stage 2 of Example 1.1) of 2,2,6-trimethyl-5-isopropenyltetrahydropyran and subsequent distillation.

2,2,6-trimethyl-5-isopropyltetrahydropyran

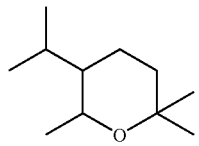

$^1$H-NMR (400 MHz, CDCl$_3$): δ=0.79 (d, J=6.9 Hz, 3H), 0.91 (d, J=7.0 Hz, 3H), 1.00-1.10 (m, 1H), 1.11-1.60 (m, 4H), 1.14 (d, J=6.1 Hz, 3H), 1.18 (s, 3H), 1.20 (s, 3H), 1.87 (dhept., J=3.2 Hz, J=6.9 Hz, 1H), 3.56 (dq, J=6.1 Hz, J=10.1 Hz, 1H) ppm.

$^{13}$C-NMR (100 MHz, CDCl$_3$): δ=15.79 (CH$_3$), 18.44 (CH$_3$), 20.05 (CH$_3$), 21.31 (CH$_3$), 22.08 (CH$_3$), 27.25 (CH), 31.74 (CH$_3$), 36.86 (CH$_2$), 47.59 (CH), 69.15 (CH), 71.36 (C) ppm.

MS: m/z (%)=170 (1) [M$^+$], 155 (21), 137 (8), 126 (22), 111 (3), 97 (5), 84 (22), 69 (36), 56 (100), 43 (30).

In accordance with Examples 1.1 and 1.2 the following compounds, inter alia, of formula (I) were manufactured:

2,6-dimethyl-5-isopropyl-2-ethyltetrahydropyran

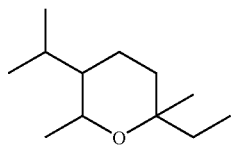

$^1$H-NMR (400 MHz, CDCl$_3$): δ=0.77 (d, J=6.9 Hz, 3H), 0.78-0.90 (m, 1 H), 0.83 (t, J=7.48 Hz, 3H), 0.90 (d, J=6.9 Hz, 3H), 1.03-1.13 (m, 1H), 1.10 (s, 3H), 1.13 (d, J=6.12 Hz, 3H), 1.25-1.48 (m, 4H), 1.55-1.61 (m, 1H), 1.79-1.89 (m, 1H), 3.44 (dq, J=6.1 Hz, J=10.0 Hz, 1H) ppm.

$^{13}$C-NMR (100 MHz, CDCl$_3$): δ=7.59 (CH$_3$), 15.83 (CH$_3$), 18.12 (CH$_2$), 20.04 (CH$_3$), 21.31 (CH$_3$), 25.93 (CH$_2$), 27.30 (CH), 27.80 (CH$_3$), 35.90 (CH$_2$), 47.31 (CH), 68.35 (CH), 72.89 (C) ppm.

MS: m/z (%)=185 (1) [MH$^+$], 169 (1), 155 (79), 137 (100), 111 (6), 97 (43), 81 (24), 70 (72), 55 (59).

2,6-dimethyl-5-isopropenyl-2-vinyltetrahydropyran

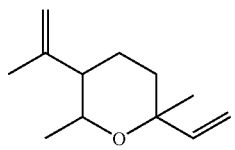

$^1$H-NMR (Blend of isomers, 400 MHz, CDCl$_3$): δ=1.08 (d, J=6.2 Hz, 3 H), 1.10 (d, J=6.1 Hz, 3H), 1.23 (s, 3H), 1.32 (s, 3H), 1.50-1.92 (m, 12 H), 1.63 (dd, J=1.0 Hz, J=1.4 Hz, 3H), 1.70 (dd, J=0.9 Hz, J=1.4 Hz, 3H), 3.62 (dq, J=6.1 Hz, J=9.9 Hz, 1H), 3.72 (dq, J=6.1 Hz, J=9.7 Hz, 1H), 4.70-4.77 (m, 2H), 4.85-5.23 (m, 2H), 5.80 (ddd, J=1.1 Hz, J=11.0 Hz, J=5.8 Hz, 2H), 5.94 (dd, J=10.8 Hz, J=17.4 Hz, 2H) ppm.

$^{13}$C-NMR (Blend of isomers, 100 MHz, CDCl$_3$): δ=20.03 (CH$_3$), 20.18 (CH$_3$), 20.28 (CH$_3$), 20.34 (CH$_3$), 25.96 (CH$_2$), 26.54 (CH$_2$), 31.18 (CH$_3$), 34.29 (CH$_2$), 34.74 (CH$_2$), 51.47 (CH), 51.56 (CH), 68.77 (CH), 70.09 (CH), 73.37 (C), 74.92 (C), 111.16 (CH$_2$), 111.47 (CH$_2$), 111.57 (CH$_2$), 114.61 (CH$_2$), 143.17 (CH), 146.36 (CH), 147.30 (C), 147.40 (C) ppm.

MS: m/z (%)=180 (1) [M$^+$], 165 (1), 136 (8), 121 (18), 107 (16), 93 (35), 79 (11), 68 (100), 53 (16).

6-isobutyl-5-isopropenyl-2,2-dimethyltetrahydropyran

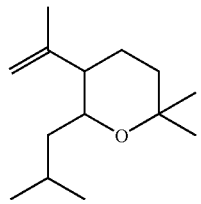

$^1$H-NMR (400 MHz, CDCl$_3$): δ=0.83 (d, J=6.6 Hz, 3H), 0.87 (d, J=6.8 Hz, 3H), 1.11-1.29 (m, 2H), 1.20 (s, 3H), 1.21 (s, 3H), 1.42-1.58 (m, 2 H), 1.67 (dd, J=0.9 Hz, J=1.4 Hz, 3H), 1.68-1.88 (m, 4H), 3.54 (dt, J=2.5 Hz, J=9.9 Hz, 1H), 4.72 (s, br., 2H) ppm.

$^{13}$C-NMR (100 MHz, CDCl$_3$): δ=20.10 (CH$_3$), 21.14 (CH$_3$), 21.89 (CH$_3$), 23.81 (CH), 23.92 (CH$_3$), 26.69 (CH$_2$), 31.75 (CH$_3$), 36.38 (CH$_2$), 42.76 (CH$_2$), 50.50 (CH), 69.95 (CH), 71.08 (C), 111.51 (CH$_2$), 147.55 (C) ppm.

MS: m/z (%)=210 (1) [M$^+$], 153 (1), 124 (22), 109 (32), 95 (6), 81 (10), 68 (100), 57 (8), 41 (21).

Example 2

Flavor Compositions and Formulation Examples

Example 2.1

Peppermint Type Flavor

| Component | Proportion [%] |
|---|---|
| 2,6-diethyl-5-isopropyl-2-methyl-tetrahydropyran | 6 |
| Anethole | 9 |
| l-menthol (natural or synthetic) | 35 |
| Peppermint oil *piperita* type (natural or reconstituted) | 20 |
| Peppermint oil *arvensis* type (natural or reconstituted) | 30 |

Example 2.2

Peppermint Type Cool Flavor

| Component | Proportion [%] |
|---|---|
| 2,6-diethyl-5-isopropyl-2-methyl-tetrahydropyran | 6 |
| Anethole | 9 |
| l-menthol (natural or synthetic) | 35 |
| Peppermint oil *piperita* type (natural or reconstituted) | 20 |

| Component | Proportion [%] |
|---|---|
| Peppermint oil *arvensis* type (natural or reconstituted) | 20 |
| 2-isopropyl-N,2,3-trimethylbutyramide (WS-23) | 2 |
| (1R,2S,5R)-N-ethyl-2-isopropyl-5-methylcyclohexane-carboxamide (WS-3) | 2 |
| Menthol propylene glycol carbonate (Frescolat MPC ®) | 2 |
| Menthol ethylene glycol carbonate (Frescolat MGC ®) | 2 |
| l-menthyl lactate (Frescolat ML ®) | 2 |

Example 2.3

Spearmint Type Flavor

| Component | Proportion [%] |
|---|---|
| 2,6-diethyl-5-isopropyl-2-methyl-tetrahydropyran | 6 |
| Anethole | 9 |
| l-menthol (natural or synthetic) | 30 |
| Peppermint oil *piperita* type (natural or reconstituted) | 5 |
| Peppermint oil *arvensis* type (natural or reconstituted) | 5 |
| l-carvone | 15 |
| Spearmint oil *cardiaca* type (natural or reconstituted) | 15 |
| Spearmint oil *spicata* type (natural or reconstituted) | 15 |

Example 2.4

Wintergreen Type Flavor

| Component | Proportion [%] |
|---|---|
| 2,6-diethyl-5-isopropyl-2-methyl-tetrahydropyran | 8 |
| Anethole | 9 |
| l-menthol (natural or synthetic) | 45 |
| Peppermint oil *piperita* type (natural or reconstituted) | 2 |
| Peppermint oil *arvensis* type (natural or reconstituted) | 3 |
| Spearmint oil *spicata* type (natural or reconstituted) | 1 |
| Eugenol | 7 |
| Eucalyptol | 5 |
| Methyl salicylate | 20 |

Example 2.5

Wintergreen Type Cool Flavor

| Component | Proportion [%] |
|---|---|
| 2,6-diethyl-5-isopropyl-2-methyl-tetrahydropyran | 6 |
| Anethole | 8 |
| 1,2-propylene glycol | 7 |
| l-menthol (natural or synthetic) | To 100 |
| Peppermint oil *piperita* type (natural or reconstituted) | 2 |
| Peppermint oil *arvensis* type (natural or reconstituted) | 3 |
| Spearmint oil *spicata* type (natural or reconstituted) | 1 |
| Eugenol | 6 |
| Eucalyptol | 4 |
| Methyl salicylate | 16 |

| Component | Proportion [%] |
|---|---|
| 2-isopropyl-N,2,3-trimethylbutyramide (WS-23) | 2 |
| (1R,2S,5R)-N-ethyl-2-isopropyl-5-methylcyclohexane-carboxamide (WS-3) | 2 |
| Menthol propylene glycol carbonate (Frescolat MPC ®) | 2 |
| Menthol ethylene glycol carbonate (Frescolat MGC ®) | 2 |
| l-menthyl lactate (Frescolat ML ®) | 2 |
| (1R,2S,5R)-N-[4-(cyanomethyl)phenyl]-2-isopropyl-5-methylcyclohexanecarboxamide | 1 |

Example 2.6

Eucalyptus Type Flavor

| Component | Proportion [%] |
|---|---|
| 2,6-diethyl-5-isopropyl-2-methyl-tetrahydropyran | 7 |
| Anethole | 18 |
| Eucalyptol | 15 |
| *Eucalyptus* oil | 5 |
| l-menthol (natural or synthetic) | 50 |
| Peppermint oil *piperita* type (natural or reconstituted) | 2 |
| Peppermint oil *arvensis* type (natural or reconstituted) | 3 |

Example 2.7

Eucalyptus Type Cool Flavor

| Component | Proportion [%] |
|---|---|
| 2,6-diethyl-5-isopropyl-2-methyl-tetrahydropyran | 4 |
| 1,2-propylene glycol | 5 |
| L-menthol methyl ether | 2 |
| Anethole | 15 |
| Eucalyptol | 15 |
| *Eucalyptus* oil | 5 |
| l-menthol (natural or synthetic) | To 100 |
| Peppermint oil *piperita* type (natural or reconstituted) | 2 |
| Peppermint oil *arvensis* type (natural or reconstituted) | 3 |
| Menthone glycerin acetal (Frescolat MGA ®) | 5 |

Example 2.8

Cinnamon Type Flavor

| Component | Proportion [%] |
|---|---|
| 2,6-diethyl-5-isopropyl-2-methyl-tetrahydropyran | 6 |
| Cinnamaldehyde | 10 |
| Anethole | 9 |
| Eugenol | 2 |
| l-menthol (natural or synthetic) | 40 |
| Peppermint oil *piperita* type (natural or reconstituted) | 10 |
| Peppermint oil *arvensis* type (natural or reconstituted) | 15 |
| Spearmint oil *spicata* type (natural or reconstituted) | 8 |

Example 2.9

Cinnamon Type Cool Flavor

| Component | Proportion [%] |
|---|---|
| 2,6-diethyl-5-isopropyl-2-methyl-tetrahydropyran | 3 |
| Menthyl methyl ether | 3 |
| Cinnamaldehyde | 10 |
| Anethole | 9 |
| Eugenol | 2 |
| l-menthol (natural or synthetic) | 40 |
| Peppermint oil *piperita* type (natural or reconstituted) | 10 |
| Peppermint oil *arvensis* type (natural or reconstituted) | 10 |
| Spearmint oil *Spicata* type (natural or reconstituted) | 8 |
| (1R,2S,5R)-N-ethyl-2-isopropyl-5-methylcyclohexane-carboxamide (WS-3) | 2 |
| (1R,2S,5R)-N-[4-(cyanomethyl)phenyl]-2-isopropyl-5-methylcyclohexanecarboxamide | 0.5 |
| (1R,2S,5R)-N-[2-(pyridin-2-yl)-ethyl]-2-isopropyl-5-methylcyclohexanecarboxamide | 0.5 |
| Menthone glycerin acetal (Frescolat MGA ®) | 1 |
| Menthol propylene glycol carbonate (Frescolat MPC ®) | 1 |

Example 2.10

Isoamylacetate Type Flavor

| Component | I (% by weight) | II (% by weight) |
|---|---|---|
| 2,6-diethyl-5-isopropyl-2-methyl-tetrahydropyran | 4 | 5 |
| Isoamylacetate | 2 | 2 |
| Ethyl butyrate | 0.5 | — |
| Butyl butyrate | — | 0.5 |
| Ethyl vanillin | 2 | — |
| Vanillin | — | 1 |
| Frambinon ™ [4-(4-hydroxyphenyl)-2-butanon] | 0.5 | 0.5 |
| l-menthol (natural) | 8 | 11 |
| Triacetin | — | 80 |
| 1,2-propylene glycol | 83 | — |

Application examples for the flavor compositions given above:

Example 2.11

Sugar-Free Chewing Gum with Cinnamon Type Cool Flavor

| Component | I (% by weight) | II (% by weight) |
|---|---|---|
| Gum base | 30.00 | 30.00 |
| Powdered sorbitol | 40.00 | To 100 |
| Powdered isomalt | 9.50 | 9.50 |
| Xylitol | 2.00 | 2.00 |
| D-mannitol | 3.00 | 3.00 |
| Aspartame | 0.10 | 0.10 |
| Acesulfame K | 0.10 | 0.10 |
| Emulgum ™ (soya-lecithin with a high phospholipid content) | 0.30 | 0.30 |
| Sorbitol (70% in water) | 13.00 | 13.00 |
| 1,2-propylene glyol | — | 1.00 |
| Glycerin | 1.00 | — |
| Pellitorine solution PLM (containing 10% pellitorine) | — | 0.035 |
| Cinnamon type cool flavor (Example 2.9) | 1.00 | 1.00 |

At a dosing of 1% of the flavor composition in chewing gum the 2,6-diethyl-5-isopropyl-2-methyl-tetrahydropyran has a distinct "boost effect" and conveys—compared with the flavor not according to the invention—a more intense feeling of freshness, in particular in the initial phase of consumption.

Example 2.12

Standard Chewing Gum

| Component | I (% by weight) | II (% by weight) |
|---|---|---|
| Gum base | 21.00 | 21.00 |
| Glucose syrup | 16.50 | 16.50 |
| Glycerin | 0.50 | 0.50 |
| Powdered sugar | 60.00 | 60.00 |
| Peppermint type flavor (Example 2.1) | 2.00 | — |
| *Eucalyptus* type cool flavor (Example 2.7) | — | 2.00 |

At a dosing of 2% of the flavor composition in chewing gum the 2.6-diethyl-5-isopropyl-2-methyl-tetrahydropyran brings about a more intense feeling of freshness and conveys—compared with the flavor not according to the invention—a greater fullness in the mouth in particular at the start of chewing.

Example 2.13

Toothpaste (Phosphate Base) with Spearmint Type Flavor

| Component | Proportion [%] |
|---|---|
| Deionized water | 36.39 |
| Glycerin | 20.00 |
| Solbrol M (sodium salt) | 0.15 |
| Sodium monofluorophosphate | 0.76 |
| Saccharin | 0.20 |
| Dicalciumphosphate dihydrate | 36.00 |
| Aerosil ® 200 (Silica) | 3.00 |
| Sodium carboxymethyl cellulose | 1.20 |
| Sodium lauryl sulfate (Texapon) | 1.30 |
| Spearmint type flavor (Example 2.3) | 1.00 |

At a dosing of 1% of the flavor composition in the toothpaste the 2.6-diethyl-5-isopropyl-2-methyl-tetrahydropyran brings about an intensified effect of the flavor when brushing and conveys—compared with the flavor not according to the invention—a distinct feeling of freshness, in particular at the start of brushing.

Example 2.14

Toothpaste (Transparent Gel Formulation)

| Component | I (% by weight) | II (% by weight) |
|---|---|---|
| Sorbitol 70% | 63.00 | To 100 |
| Deionized water | 11.31 | 11.31 |
| Saccharin | 0.20 | 0.20 |
| Sodium monofluorphosphate | 1.14 | 1.14 |
| Solbrol | 0.15 | 0.15 |
| Trisodium phosphate | 0.10 | 0.10 |
| PEG 1500 (PEG 32) | 5.00 | 5.00 |
| Sident 9 (abrasive silica) | 8.00 | 8.00 |
| Sident 22 S (thickening silica) | 8.00 | 8.00 |
| Sodium carboxymethyl cellulose | 0.60 | 0.60 |
| Sodium lauryl sulfate | 1.50 | 1.50 |
| Cinnamon type flavor (Example 2.8) | 1.00 | — |
| Wintergreen type cool flavor (Example 2.5) | — | 1.00 |
| Pellitorine solution PLM (containing 10% pellitorine) | — | 0.025 |

At a dosing of 1% of the flavor composition in the toothpaste during brushing, as a result of the 2.6-Diethyl-5-isopropyl-2-methyl-tetrahydropyran, the paste acquires a clearer freshness profile and conveys—compared with the flavor not according to the invention—a distinct retronasal cooling.

Example 2.15

Toothpaste ('Silica Opaque')

| Component | I (% by weight) | II (% by weight) | III (% by weight) |
|---|---|---|---|
| Deionized water | 26.53 | 26.53 | 26.53 |
| Sorbitol 70% | 45.00 | To 100 | To 100 |
| Solbrol M Na-salt | 0.15 | 0.15 | 0.15 |
| Trisodium phosphate | 0.10 | 0.10 | 0.10 |
| Saccharin | 0.20 | 0.20 | 0.20 |
| Sodium monoflurophosphate | 1.12 | 1.12 | 1.12 |
| PEG 1500 | 5.00 | 5.00 | 5.00 |
| Sident 9 (abrasive Silica) | 10.00 | 10.00 | 10.00 |
| Sident 22 S (thickening Silica) | 8.00 | 8.00 | 8.00 |
| Sodium carboxymethyl cellulose | 0.90 | 0.90 | 0.90 |
| Titanium (IV) oxide | 0.50 | 0.50 | 0.50 |
| Sodium lauryl sulfate (SLS) | 1.50 | 1.50 | 1.50 |
| Pellitorine solution PLM (containing 10% pellitorine) | — | 0.025 | — |
| Peppermint type cool flavor (Example 2.2) | 1.00 | 1.00 | — |
| Isoamylacetate I type flavor (Example 2.10) | — | — | 0.70 |

At a dosing of 1% of the flavor composition in the toothpaste during brushing as a result of the 2.6-diethyl-5-isopropyl-2-methyl-tetrahydropyran the paste acquires increased fullness in the mouth and achieves—compared with the flavor not according to the invention—a fresher feeling in the mouth. Toothpaste III is particularly suitable as a toothpaste for children.

Example 2.16

Toothpaste (Calcium Carbonate Base) with Eucalyptus Type Cool Flavor

| Component | I (% by weight) | II (% by weight) |
|---|---|---|
| Deionized water | 27.50 | To 100 |
| Saccharin | 0.20 | 0.20 |
| Solbrol M sodium salt | 0.20 | 0.20 |
| Sodium monofluorphosphate | 0.80 | 0.80 |
| Sorbitol 70% | 29.00 | 29.00 |
| Calcium carbonate | 35.00 | 35.00 |
| Sident 22 S (thickening silica) | 2.50 | 2.50 |
| Sodium carboxymethyl cellulose | 1.30 | 1.30 |
| Titanium dioxide | 0.50 | 0.50 |
| Sodium lauryl sulfate | 2.00 | 2.00 |
| *Eucalyptus* type cool flavor (Example 2.7) | 1.00 | 1.00 |
| Pellitorine solution PLM (containing 10% pellitorine) | — | 0.020 |

At a dosing of 1% of the flavor composition in this toothpaste the sensorial profile improves considerably—compared with the flavor not according to the invention—and the taste impression satisfies through greater freshness.

Example 2.17

Mouthwash Concentrate with Wintergreen Type Flavor

| Component | Proportion [%] |
|---|---|
| Ethyl alcohol 96% | 42.00 |
| Cremophor RH 455 | 5.00 |
| Deionized water | 48.67 |
| Allantoin | 0.20 |
| Sodium saccharin 450 | 0.10 |
| Color L-Blue 5000 (1% in water) | 0.03 |
| Wintergreen type flavor (Example 2.4) | 4.00 |

At a dosing of 4% of the flavor composition in this mouthwash there is a satisfying improvement in the taste—compared with the flavor not according to the invention—due to a stronger and faster cooling in the oral cavity.

Example 2.18

Mouthwash (Ready to Use, Alcohol-Free) with Eucalyptus Type Flavor

| Component | I (% by weight) | II (% by weight) |
|---|---|---|
| Cremophor RH 455 | 1.80 | 1.80 |
| Deionized water | 87.57 | To 100 |

Example 2.19

Mouthwash (Ready to Use, with Alcohol)

| Component | I (% by weight) | II (% by weight) |
|---|---|---|
| Sorbitol 70% | 10.00 | 10.00 |
| Sodium fluoride | 0.18 | 0.18 |
| Sodium saccharin 450 | 0.10 | 0.10 |
| Solbrol M sodium salt | 0.15 | 0.15 |
| *Eucalyptus* type flavor (Example 2.6) | 0.2 | 0.2 |
| Pellitorine solution PLM (containing 10% pellitorine) | — | 0.0125 |

| Component | I (% by weight) | II (% by weight) | III (% by weight) |
|---|---|---|---|
| Ethyl alcohol 96% | 10.00 | 5.00 | 7.00 |
| Cremophor CO 40 | 1.00 | 1.00 | 1.00 |
| Benzoic acid | 0.10 | 0.12 | 0.10 |
| Deionized water | 83.46 | To 100 | To 100 |
| Sorbitol 70% | 5.00 | 1.00 | 5.00 |
| Sodium saccharin 450 | 0.07 | 0.05 | 0.05 |
| L-Blue 5000 (1% in water) | 0.10 | 0.10 | 0.10 |
| Glycerin | — | 8.00 | — |
| 1,2-propylene glycol | — | 2.00 | 3.00 |
| Cetylpyridinium chloride | — | — | 0.07 |
| Hydrogen peroxide (35% $H_2O_2$ in water) | — | 3.00 | 4.00 |
| Wintergreen type flavor cool (Example 2.5) | 0.25 | — | — |
| *Eucalyptus* type flavor cool (Example 2.7) | — | 0.25 | 0.05 |
| Isoamylacetate II type flavor (Example 2.10) | — | — | 0.30 |

Example 2.20

Hardboiled Candy, Sugar-Free

| Component | I (% by weight) | II (% by weight) | II (% by weight) |
|---|---|---|---|
| Water | 2.24 | 2.24 | 2.24 |
| Isomalt | 94.98 | To 100 | To 100 |
| Xylitol | 2.40 | 2.40 | 2.40 |
| Sucralose | 0.03 | 0.03 | 0.03 |
| Acesulfame K | 0.050 | 0.050 | 0.050 |
| Citric acid | 0.050 | 0.050 | 0.050 |
| Pellitorine solution PLM (containing 10% pellitorine) | — | 0.0075 | 0.010 |
| Isoamylacetate II type flavor (Example 2.10) | — | — | 0.20 |
| Peppermint type flavor (Example 2.1) | 0.25 | 0.20 | — |

Example 2.21

Hardboiled Candy

| Component | I (% by weight) | II (% by weight) | III (% by weight) |
|---|---|---|---|
| Water | 2.75 | 2.50 | 2.50 |
| Sugar | 60.1 | To 100 | To 100 |
| Glucose syrup | 36.9 | 36.0 | 36.0 |
| Maltose | — | 2.00 | 2.00 |
| Palm kernel oil | — | 0.80 | 0.80 |
| Citric acid | — | 0.25 | 0.25 |
| Ginseng extract | — | 0.40 | 0.40 |
| Blue coloring | — | 0.01 | 0.01 |
| Spearmint type flavor (Example 2.3) | 0.25 | 0.35 | — |
| Isoamylacetate I type flavor (Example 2.10) | — | — | 0.175 |

Example 2.22

Tooth Crème and Mouthwash as a 2-in-1 Product

| Component | I (% by weight) | II (% by weight) |
|---|---|---|
| Ethanol, 96% | 5.00 | 5.00 |
| Sorbitol, 70% in water | 40.00 | 40.00 |
| Glycerin | 20.00 | 20.00 |
| Saccharin | 0.20 | 0.20 |
| Na-monofluorophosphate | 0.76 | 0.76 |
| Solbrol M, Na-salt | 0.15 | 0.15 |
| Abrasive silica (Sident 9) | 20.00 | 20.00 |
| Thickening silica (Sident 22S) | 2.00 | 2.00 |
| Na-carboxymethylcellulose | 0.30 | 0.30 |
| Sodium lauryl sulfate | 1.20 | 1.20 |
| Green coloring (1% in water) | 0.50 | 0.50 |
| *Eucalyptus* type cool flavor (Example 2.7) | 1.00 | — |
| Natural peppermint oil arvensis (containing 68% by weight of l-menthol) | — | 1.12 |
| 2,6-diethyl-5-sec.-butyl-2-methyltetrahydropyran | — | 0.08 |
| Distilled water | To 100 | To 100 |

Example 2.23

Instant Drink Powder

| Component | I (% by weight) | II (% by weight) |
|---|---|---|
| Sugar (sucrose) | To 100 | To 100 |
| Citric acid | 11.58 | 11.58 |
| Trisodium citrate | 0.70 | 0.70 |
| Tricalcium phosphate | 0.60 | 0.60 |
| Vitamin C | 0.66 | 0.66 |
| Grindsted ® JU 543 stabilizer system (Danisco) | 0.90 | 0.90 |
| Saccharin | 0.561 | 0.561 |
| Lemon flavor spray-dried | 1.75 | — |
| Orange flavor spray-dried | — | 1.85 |
| Peppermint type cool flavor (Example 2.2), spray-dried on maltodextrin (DE 18), dextrose gum Arabic, flavor loading 35% | 1.75 | — |
| Cinnamon type cool flavor (Example 2.9), spray-dried on maltodextrin (DE 15-19) and gum Arabic, flavor loading 40% | — | 1.20 |

45 g of this drink powder were dissolved in 1,000 ml whilst stirring. The drink obtained had a refreshing, cooling taste of lemons and peppermints (variant I) or a refreshing, cooling taste of orange, cinnamon and mint (variant II).

Example 2.24

Throat Sweets with Viscous Liquid Center (Center-Filled Hard Candy) with Cinnamon Type Flavor And Cinnamon Type Cool Flavor

|  | I (% by weight) | II (% by weight) |
|---|---|---|
| Mixture A (shell) (80% of the candies) | | |
| Sugar (sucrose) | 58.12 | 49.37 |
| Glucose syrup (solid content 80%) | 41.51 | 49.37 |
| Cinnamon type flavor (Example 2.8) | 0.17 | 0.25 |
| l-menthol | 0.10 | — |
| Lemon oil | 0.10 | 0.10 |
| Citric acid | — | 0.91 |
| Total: | 100 | 100 |
| Mixture B (center) (20% of the candies) | | |
| High fructose corn syrup (solid sugar content 85%, just 15% water) | 84.355 | 84.31 |
| Glycerin | 15.0 | 15.0 |
| Lecithin | 0.02 | 0.02 |
| Cinnamon oil | — | 0.27 |
| Cinnamon type cool flavor (Example 2.9) | 0.28 | — |
| 2,6-diethyl-5-sec.-butyl-2-methyltetrahydro-pyran | — | 0.05 |
| Capsaicin | 0.025 | — |
| Piperine | 0.05 | 0.05 |
| Vanillyl alcohol-n-butyl ether | — | 0.10 |
| Red coloring as 2.5% aqueous solution | 0.20 | 0.20 |
| Vanillin | 0.07 | — |
| Total | 100 | 100 |

In accordance with U.S. Pat. No. 6,432,441 (Example 1 there) and the methods described in U.S. Pat. No. 5,458,894 or U.S. Pat. No. 5,002,791 candies with a viscous liquid center were manufactured. The two mixtures A and B were processed separately into bases for the shell (mixture A) and the center (mixtures B), respectively. In affected persons the filled throat sweets obtained by co-extrusion acted against coughs, sore throats and hoarseness.

Example 2.25

Gelatin Capsules for Direct Consumption

|  | I (% by weight) | II (% by weight) | III (% by weight) |
|---|---|---|---|
| Gelatin shell: | | | |
| Glycerin | 2.014 | 2.014 | 2.014 |
| Gelatin 240 Bloom | 7.91 | 7.91 | 7.91 |
| Aspartame | 0.05 | — | — |
| Sucralose | 0.035 | 0.050 | 0.070 |
| Allura Red (red coloring) | 0.006 | 0.006 | 0.006 |
| Brilliant Blue (blue coloring) | — | — | 0.006 |
| Core composition: | | | |
| Vegetable oil triglyceride (coconut oil fraction) | To 100 | To 100 | To 100 |

|  | I (% by weight) | II (% by weight) | III (% by weight) |
|---|---|---|---|
| Flavor G | 9.95 | — | 7.5 |
| Peppermint type cool flavor (Example 2.2) | — | 15.0 | 18.5 |
| 2,6-diethyl-5-isopropyl-2-methyl-tetrahydropyran | 0.60 | — | — |

Here flavor G had the following composition (figures in each case in % by weight): 0.1% Neotame powder, 29.3% peppermint oil arvensis, to 100% peppermint piperita oil Willamette, 2.27% sucralose, 0.7% clove bud oil, 2.28% triacetin, 5.4% diethyl tartrate, 12.1% peppermint oil yakima, 0.7% ethanol, 3.36% 2-hydroxyethyl menthyl carbonate, 2.6% 2-hydroxypropyl menthyl carbonate, 5.77% D-limonene, 5.67% L-menthyl acetate, 0.4% vitamin E-acetate.

The gelatin capsules I, II and II for direct consumption were manufactured in accordance with WO 2004/050069 and in each case had a diameter of mm, with a weight ratio of the core material to the shell material of 90:10. The capsules opened in the mouth in each case within less than 10 seconds and dissolved completely within less than 50 seconds.

Example 2.26

Chewing Gum (with Sugar and Sugar-Free)

|  | I (% by weight) | II (% by weight) | III (% by weight) |
|---|---|---|---|
| Chewing gum base | 21.0 | 30.0 | 30.0 |
| Glycerin | 0.5 | 1.0 | 1.0 |
| Menthol spearmint *eucalyptus* flavor P1 | 1.0 | 1.4 | 1.4 |
| Glucose syrup | 16.5 | — | — |
| Powdered sugar | To 100 | — | — |
| 2,6-diethyl-5-isopropyl-2-methyl-tetrahydropyran | — | — | 0.15 |
| 2,6-dimethyl-5-isopropyl-2-ethyltetrahydro-pyran | 0.10 | — | — |
| 2,6-diethyl-5-sec.-butyl-2-methyltetrahydro-pyran | — | 0.125 | — |
| Sorbitol (in powder form) | — | To 100 | To 100 |
| Palatinite | — | 9.5 | 9.5 |
| Xylitol | — | 2.0 | 2.0 |
| Mannitol | — | 3.0 | 3.0 |
| Aspartame | — | 0.1 | 0.1 |
| Acesulfame K | — | 0.1 | 0.1 |
| Emulgum ™ (emulsifier) | — | 0.3 | 0.3 |
| Sorbitol 70%, in water | — | 14.0 | 14.0 |

Flavor P1 had the following composition (figures in each case in % by weight):

0.05% isobutyraldehyde, 0.05% 3-octanol, 0.05% dimethyl sulfide, 0.1% trans-2-hexenal, 0.1% cis-3-hexenol, 0.1% natural 4-terpineol, 0.1% isopulegol, 0.2% natural piperitone, 0.3% linalool, 1.0% isoamyl alcohol, 1.0% isovaleraldehyde, 2.5% natural alpha-pinene, 2.5% natural beta-pinene, 8.0% eucalyptol, 7.0% 1-menthyl acetate, 12.0% l-menthone, 5.0% isomenthone, 20.5% l-carvone, 39.45% l-menthol.

Example 2.27

Sugar-Free Chewing Gum

The chewing gum base comprised 2.0% butyl rubber (isobutene-isoprene copolymer, MW 400,00), 400000), 6.0% polyisobutene (MW=43,800), 43.5% polyvinyl acetate (MW=12,000), 31.5% polyvinyl acetate (MW=47.000), 6.75% triacetin and 10.25% calcium carbonate. The manufacture of the chewing gum base K1 and of the chewing gum can take place similarly to U.S. Pat. No. 5,601,858.

|  | I (% by weight) | II (% by weight) | III (% by weight) |
|---|---|---|---|
| Chewing gum base K1 | 26.00 | 27.00 | 26.00 |
| Triacetin | 0.25 | 0.25 | 0.25 |
| Lecithin | 0.50 | 0.50 | 0.50 |
| Sorbitol, crystalline | To 100 | To 100 | To 100 |
| Mannitol | 15.30 | 15.20 | 15.10 |
| Glycerin | 12.10 | 12.00 | 11.80 |
| Saccharin-Na | 0.17 | — | 0.10 |
| Encapsulated aspartame | 1.08 | 1.18 | 1.08 |
| Amorphous silica | 1.00 | 1.00 | 1.00 |
| Cotton seed oil | 0.50 | 0.50 | 0.50 |
| Polyoxyethylene sorbitan monolaurate (E-432) | 1.00 | 1.00 | 1.00 |
| Encapsulated l-carvone (loading: 30%) | — | 0.20 | — |
| Wintergreen type cool flavor (Example 2.5). | 1.00 | — | 1.70 |
| *Eucalyptus* type cool flavor (Example 2.7) | 0.50 | 1.40 | — |
| 2,6-dimethyl-5-isopropyl-2-ethyltetrahydro-pyran | — | 0.10 | — |
| l-menthyl-l-lactate | — | — | 0.20 |

Example 2.28

Sugar-Free Chewing Gum

The chewing gum base K2 comprised 28.5% terpene resin, 33.9% polyvinyl acetate (MW=14,000), 16.25% hydrogenated vegetable oil, 5.5% mono- and diglycerides, 0.5% polyisobutene (MW 75,000), 2.0% butyl rubber (isobutene isoprene copolymer), 4.6% amorphous silicon dioxide (water content approximately 2.5%), 0.05% antioxidant tert.-butyl hydroxy toluene (BHT), 0.2% lecithin and 8.5% calcium carbonate. Manufacture of the chewing gum base can take place similarly to U.S. Pat. No. 6,986,907.

|  | I (% by weight) | II (% by weight) | III (% by weight) |
|---|---|---|---|
| Chewing gum base K2 | 25.30 | 27.30 | 26.30 |
| Sorbitol | To 100 | To 100 | To 100 |
| Glycerin | 2.40 | 2.40 | 2.40 |
| Lecithin | 7.00 | 7.00 | 7.00 |
| Aspartame | 0.14 | 0.14 | 0.14 |
| Encapsulated aspartame | 0.68 | 0.68 | 0.68 |
| Menthol, spray-dried (loading: 25%) | 0.50 | — | 0.50 |
| Cherry flavor, spray-dried (contains benzaldehyde) | — | 1.00 | — |
| Peppermint type flavor (Example 2.1), spray-dried, flavor content 30% | 1.50 | 1.70 | — |
| Cinnamon type cool flavor (Example 2.9) | 1.00 | — | 1.50 |

The chewing gums in recipe (I) and (II) were manufactured in strip form, and those in recipe (III) in tablet form and then coated with xylitol.

Example 2.29

Tooth Cream with Bleaching Effect

|  | I (% by weight) | II (% by weight) | III (% by weight) |
|---|---|---|---|
| Polyphosphate (Glass H, (n ≈ 21), Astaris) | 7.00 | 7.00 | 7.00 |
| Calcium peroxide | 1.00 | — | 2.50 |
| Na-percarbonate | — | 11.00 | — |
| Poloxamer 407 | 5.00 | 2.00 | 5.00 |
| Polyethylene glycol | 3.00 | — | 3.00 |
| Sorbitol, 70% in water | — | 22.00 | — |
| Glycerin | 43.80 | 12.50 | 28.60 |
| 1,2-propylene glycol | 4.00 | — | 2.50 |
| Na-saccharin | 0.40 | 0.20 | 0.50 |
| Sodium bicarbonate | — | 5.00 | 15.00 |
| Sodium carbonate | 2.00 | 2.00 | 2.00 |
| Silica | 20.00 | 22.00 | 20.00 |
| Na-carboxymethylcellulose | 0.60 | 0.55 | 0.30 |
| Sodium lauryl sulfate | 1.00 | 4.00 | 2.00 |
| Xanthan Gum | 0.20 | 0.20 | 0.20 |
| Titanium dioxide (anatas) | 0.50 | 0.50 | 0.50 |
| *Eucalyptus* type cool flavor (Example 2.7) | 1.00 | — | — |
| Cinnamon type cool flavor (Example 2.9) | — | 1.25 | — |
| Peppermint type cool flavor (Example 2.2) | — | — | 1.50 |
| Distilled water | To 100 | To 100 | To 100 |

Example 2.30

Tooth Crèmes with Tin and Zinc Salts

|  | I (% by weight) | II (% by weight) | III (% by weight) |
|---|---|---|---|
| Sodium fluoride NaF | 0.42 | 0.50 | — |
| Tin fluoride $SnF_2$ | — | 0.90 | 0.95 |
| Tin chloride $SnCl_2$ | 1.50 | — | 2.00 |
| Zinc lactate | 2.00 | 2.00 | — |
| Zinc carbonate $ZnCO_3$ | — | 1.00 | 1.50 |
| Na-gluconate | — | 0.67 | 1.50 |
| Poloxamer 407 | 14.50 | — | — |
| Polyethylene glycol | 1.00 | 3.00 | — |
| Sorbitol, 70% in water | — | 38.00 | 37.50 |
| Glycerin | 37.50 | 5.00 | 14.40 |
| 1,2-propylene glycol | 7.00 | 5.00 | — |
| Na-saccharin | 0.30 | 0.50 | 0.50 |
| Abrasive silica | 20.00 | 22.50 | 25.00 |
| Sodium hydroxide | — | 0.10 | 0.20 |
| Sodium lauryl sulfate | — | 2.00 | 1.50 |
| Na-polyphosphate | — | — | 4.00 |
| Tetrasodium pyrophosphate | 1.00 | 2.50 | — |
| Coloring (1% in water) | 0.40 | 0.50 | 0.50 |
| *Eucalyptus* type cool flavor (Example 2.7) | 0.95 | — | — |
| Cinnamon type cool flavor (Example 2.9) | — | 1.20 | — |
| Peppermint type cool flavor (Example 2.2) | — | — | 1.15 |
| Distilled water | To 100 | To 100 | To 100 |

The invention claimed is:
1. An alkylated tetrahydropyran of formula (I)

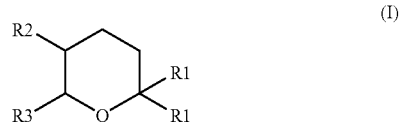

(I)

wherein:
one R1 is a branched or unbranched alkyl residue with from 1 to 3 C-atoms or a branched or unbranched alkenyl residue with 2 or 3 C-atoms and the other R1 is a branched or unbranched alkyl residue with 2 or 3 C-atoms or a branched or unbranched alkenyl residue with 2 or 3 C-atoms;

R2 is a branched or unbranched alkyl or an alkenyl residue with 3 or 4 C-atoms; and R3 is a branched or unbranched alkyl residue with from 1 to 5 C-atoms.

2. The alkylated tetrahydropyran of claim 1, wherein: one R1 is a methyl, ethyl or vinyl residue and the other R1 is an ethyl or vinyl residue; R2 is an isopropyl, isopropenyl, sec-butyl or sec-butenyl residue; and R3 is an unbranched alkyl residue with from 1 to 3 C-atoms.

3. The alkylated tetrahydropyran of claim 1, wherein: one R1 is a methyl or ethyl residue and the other R1 is an ethyl or vinyl residue; R2 is an isopropyl or sec-butyl residue; and R3 is a methyl or ethyl residue.

4. The alkylated tetrahydropyran of claim 1, selected from the group consisting of 2,6-diethyl-5-isopropyl-2-methyltetrahydropyran, 6-ethyl-5-isopropenyl-2-methyl-2-vinyltetrahydropyran, 2,6-dimethyl-5-isopropyl-2-ethyltetrahydropyran, 2,6-dimethyl-5-isopropenyl-2-vinyltetrahydropyran, 2,6-diethyl-5-sec.-butyl-2-methyltetrahydropyran and 2,6-dimethyl-5-sec.-butyl-2-ethyltetrahydropyran.

5. A mixture comprising:
a) one or more alkylated tetrahydropyrans according to claim 1;
b) one or more (volatile) flavoring substance(s) and/or flavoring(s) selected from the group consisting of substances with a physiological cooling action, flavoring substances without a physiological cooling action, substances with a trigeminal or mouthwatering effect without a physiological cooling action and taste-modulating substances; and optionally
c) a cosmetically or pharmaceutically acceptable carrier.

6. The mixture of claim 5, wherein:
the one or more substances with a physiological cooling action is/are selected from the group comprising 1-menthol, isopulegol, menthone glycerin acetal, menthyl lactate, substituted menthane-3-carboxylic acid amides, substituted N-aryl-menthane-3-carboxylic acid amides, substituted N-alkyl-menthane-3-carboxylic acid amides, 2-isopropyl-N, 2,3-trimethyl butanamide, substituted cyclohexane carboxylic acid amides, 3-menthoxy-1,2-propandiol, 2-hydroxyethyl menthyl carbonate, 2-hydroxy propyl menthyl carbonate, N-acetyl glycin menthyl ester, menthyl hydroxycarboxylic acid esters, menthyl monosuccinate, menthylmonoglutarate, 2-mercaptocyclodecanon, menthyl-2-pyrrolidin-5-one carboxylate, [N-(4-cyanomethylphenyl)-p-menthane carboxamide], (1R,2S,5R)-2-isopropyl-5-methyl-N-(2-(pyridin-2-yl)ethyl)cyclohexane carboxamide, WS-3, WS-23, WS-5, WS-12, WS-14, TPG1, frescomenthe, p-menthane-3,8-diol, N,N-dimethyl menthyl succinamide, 6-isopropyl-3,9-dimethyl-1,4-dioxaspiro[4.5]decan-2-one, icilin and icilin derivates, cubebol, menthyl oxamate, menthyl-N-methyloxamate, menthyl-N,N-dimethyloxamate, menthyl-N-ethyloxamate, menthyl-N,N-diethyloxamate, menthyl-N-propyloxamate, menthyl-N,N-dipropyloxamate, menthyl-N-isopropyloxamate, menthyl-N,N-diisopropyloxamate, menthyl-N-cyclopropyloxamate, menthyl-N-butyloxamate, morpholin-4-yl-oxo-acetic acid-(1R,2S,5R)-2-isopropyl-5-methyl-cyclohexyl ester, menthyl-N-(2-methoxyethyl)-oxamate, menthyl-N-(3-methoxypropyl)-oxamate, menthyl-N-(2-hydroxyethyl)-oxamate, and menthyl-N-(3-hydroxypropyl)-oxamate;
the one or more of the flavoring substances without a physiological cooling action is/are substances which bring about a spicy taste or a sensation of hotness or heat on the skin and mucous membranes or prickling or tingling sensation in the oral cavity and pharyngeal cavity.

7. The mixture of claim 5, wherein one or more of the substances in component b) brings about a taste effect.

8. The mixture of claim 5, wherein one or more of the substances in component b) brings about no taste effect.

9. A preparation for oral hygiene use or pleasure, pharmaceutical use, or cosmetic use comprising one or more alkylated tetrahydropyrans according to claim 1.

10. The preparation for oral hygiene use or pleasure, pharmaceutical use, or cosmetic use of claim 9 that
achieves a physiological cooling action on the skin and/or a mucous membrane; and/or
conveys, modifies, or intensifies a feeling of freshness in the mouth, throat and/or respiratory tract.

11. The preparation of claim 10, wherein the preparation:
(i) is a preparation for nutrition or pleasure selected from baked goods, confectionery, alcoholic or non-alcoholic drinks, instant drinks, meat products, eggs or egg products, cereal products, milk products, fruit preparations, vegetable preparations, snack items, fat- and oil-based products or emulsions of these, other convenience foods and soups, spices, spice mixes, seasonings, semi-finished goods, food supplements; or
(ii) is a preparation for oral hygiene and selected from the group consisting of: toothpaste, tooth creme, tooth gel, tooth powder, tooth cleaning fluid, tooth cleaning foam, mouthwash, tooth creme and mouthwash as a 2-in-1 product, hard candy, mouth spray, dental floss and dental care chewing gum; or
(iii) is a pharmaceutical preparation; or
(iv) is a cosmetic preparation, selected from the group consisting of: soap, syndet, liquid wash, shower or bath preparation, emulsion, ointment, paste, gel, oil, toner, balsam, serum, powder, eau de toilette, toilette, eau de Cologne, perfume, wax, stick, roll-on, (pump)-spray, aerosol (foaming, non-foaming or after-foaming), foot care product, beard shampoo or care preparation, insect repellent, sunscreen preparation, aftersun preparation, shaving preparation, aftershave, depilatory product, hair care product, conditioner, hair tonic, hair lotion, hair rinse, hair cream, pomade, permanent wave and setting lotion, hair smoothing product, hair strengthener, styling aid, blonding product, hair lightener, hair conditioner, hair mousse, hair toning product, nail care product, deodorant, antiperspirant, mouthwash, oral douche, make-up, make-up remover, eye care cream, lip cosmetics, lip care preparation, decorative cosmetics, bath product and face mask.

12. A method for providing a cooling sensation on the skin and/or a mucous membrane comprising administering to the skin and/or mucous membrane an alkylated tetrahydropyran of claim 1 in a sufficient amount to impart a cooling sensation.

13. A method for providing a cooling sensation on the skin and/or a mucous membrane comprising administering to the skin and/or mucous membrane a mixture of claim 5 in a sufficient amount to impart a cooling sensation.

14. A method for treating or alleviating a cough, a cold, inflammation, a sore throat, or hoarseness comprising administering to an individual an alkylated tetrahydropyran of claim 1 in a sufficient amount to treat or alleviate the symptoms associated with a cough, a cold, inflammation, a sore throat, or hoarseness.

15. A method for treating or alleviating a cough, a cold, inflammation, a sore throat, or hoarseness comprising administering to an individual an alkylated tetrahydropyran of claim 4 in a sufficient amount to treat or alleviate the symptoms associated with a cough, a cold, inflammation, a sore throat, or hoarseness.

16. A method for treating or alleviating a cough, a cold, inflammation, a sore throat, or hoarseness comprising administering to an individual a mixture of claim 5 in a sufficient amount to treat or alleviate the symptoms associated with a cough, a cold, inflammation, a sore throat, or hoarseness.

17. A method for conveying, modifying or intensifying a feeling of freshness in the mouth and/or the respiratory tract comprising administering a compound of claim 1 to the mouth and/or the respiratory tract in a sufficient amount to convey, modify, or intensify a feeling of freshness.

18. A method for conveying, modifying or intensifying a feeling of freshness in the mouth and/or the respiratory tract comprising administering a compound of claim 4 to the mouth and/or the respiratory tract in a sufficient amount to convey, modify, or intensify a feeling of freshness.

19. A method for conveying, modifying or intensifying a feeling of freshness in the mouth and/or the respiratory tract comprising administering a mixture of claim 5 to the mouth and/or the respiratory tract in a sufficient amount to convey, modify, or intensify a feeling of freshness.

20. A method for manufacturing an alkylated tetrahydropyran of formula (I):

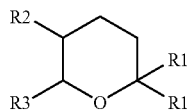

(I)

wherein:
one R1 is a branched or unbranched alkyl residue with from 1 to 3 C-atoms or a branched or unbranched alkenyl residue with 2 or 3 C-atoms and the other R1 is a branched or unbranched alkyl residue with 2 or 3 C-atoms or a branched or unbranched alkenyl residue with 2 or 3 C-atoms;
R2 is a branched or unbranched alkyl or an alkenyl residue with 3 or 4 C-atoms; and
R3 is a branched or unbranched alkyl residue with from 1 to 5 C-atoms;
comprising:
converting the aldehyde (B) with the alcohol component (A) and deriving the corresponding cyclized tetrahydropyran compound (C); and
if necessary reducing the tetrahydropyran compound (C) to the tetrahydropyran compound (D)

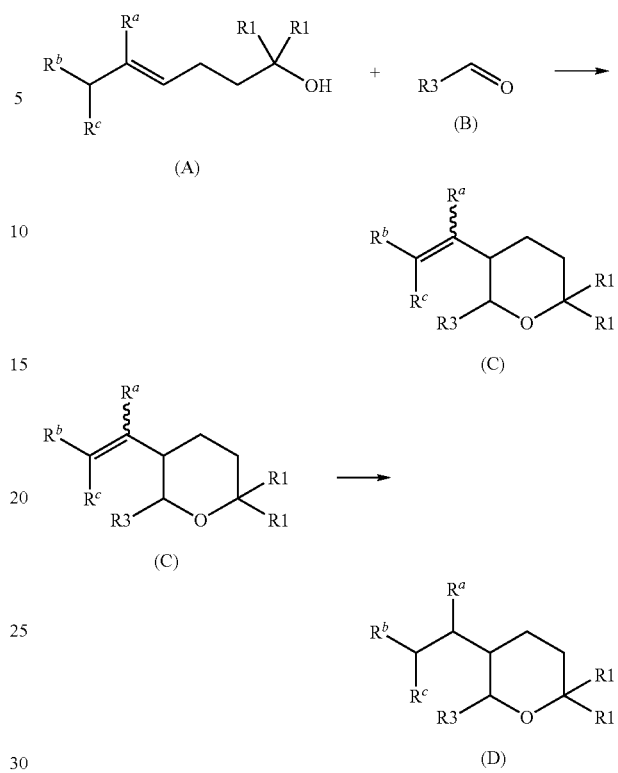

wherein:
R1 and R3 are as defined above; and
$R^a$, $R^b$ and $R^c$ independently of one another represent hydrogen, methyl or ethyl, provided that $R^a$, $R^b$ and $R^c$ in total contain 1 or 2 C-atoms.

21. The preparation of claim 11 wherein the preparation is an oral or nasal pharmaceutical preparation to be swallowed or chewed, further wherein said preparation is in the form of capsules, tablets, sugar-coated pills, granulates, pellets, solid mixtures, dispersions in liquid phases, emulsions, powders, solutions or pastes.

* * * * *